United States Patent
Chernyak

(10) Patent No.: US 12,201,560 B2
(45) Date of Patent: Jan. 21, 2025

(54) FEMTOSECOND LASER SYSTEM AND METHODS FOR PHOTOREFRACTIVE KERATECTOMY

(71) Applicant: AMO DEVELOPMENT, LLC, Irvine, CA (US)

(72) Inventor: Dimitri A. Chernyak, Belmont, MA (US)

(73) Assignee: AMO Development, LLC, Irvine, CA (US)

( * ) Notice: Subject to any disclaimer, the term of this patent is extended or adjusted under 35 U.S.C. 154(b) by 105 days.

(21) Appl. No.: 18/064,194

(22) Filed: Dec. 9, 2022

(65) Prior Publication Data
US 2023/0106593 A1    Apr. 6, 2023

Related U.S. Application Data

(62) Division of application No. 15/795,124, filed on Oct. 26, 2017, now Pat. No. 11,529,259.

(51) Int. Cl.
*A61F 9/008* (2006.01)

(52) U.S. Cl.
CPC ........ *A61F 9/00827* (2013.01); *A61F 9/0084* (2013.01); *A61F 9/00836* (2013.01); *A61F 2009/00846* (2013.01); *A61F 2009/00848* (2013.01); *A61F 2009/00851* (2013.01); *A61F 2009/00853* (2013.01); *A61F 2009/0087* (2013.01); *A61F 2009/00872* (2013.01); *A61F 2009/00897* (2013.01)

(58) Field of Classification Search
CPC ............... A61F 9/00827; A61F 9/0084; A61F 9/00836; A61F 2009/00846; A61F 2009/00848; A61F 2009/00851; A61F 2009/00853; A61F 2009/0087; A61F 2009/00872; A61F 2009/00897
USPC .......................................................... 606/5
See application file for complete search history.

(56) References Cited

U.S. PATENT DOCUMENTS

| | | | |
|---|---|---|---|
| 4,665,913 | A | 5/1987 | L'Esperance, Jr. |
| 4,669,466 | A | 6/1987 | L'Esperance |
| 4,732,148 | A | 3/1988 | L'Esperance, Jr. |
| 4,764,930 | A | 8/1988 | Bille et al. |
| 4,770,172 | A | 9/1988 | L'Esperance, Jr. |
| 4,773,414 | A | 9/1988 | L'Esperance, Jr. |
| 5,108,388 | A | 4/1992 | Trokel et al. |
| 5,163,934 | A | 11/1992 | Munnerlyn |
| 5,207,668 | A | 5/1993 | L'Esperance, Jr. |
| 5,219,343 | A | 6/1993 | L'Esperance, Jr. |

(Continued)

FOREIGN PATENT DOCUMENTS

| | | |
|---|---|---|
| WO | 2009158723 A2 | 12/2009 |
| WO | 2013126653 A1 | 8/2013 |
| WO | 2016049442 A1 | 3/2016 |

*Primary Examiner* — Aaron F Roane

(57) ABSTRACT

Embodiments of this invention generally relate to ophthalmic laser procedures and, more particularly, to systems and methods for lenticular laser incision. In an embodiment, an ophthalmic surgical laser system comprises a laser delivery system for delivering a pulsed laser beam to a target in a subject's eye, an XY-scan device to deflect the pulsed laser beam, a Z-scan device to modify a depth of a focus of the pulsed laser beam, and a controller configured to form a top lenticular incision and a bottom lenticular incision of a lens in the subject's eye, or just a bottom lenticular incision.

11 Claims, 8 Drawing Sheets

(56) References Cited

U.S. PATENT DOCUMENTS

| | | |
|---|---|---|
| 5,646,791 A | 7/1997 | Glockler |
| 5,748,352 A | 5/1998 | Hattori |
| 5,993,438 A | 11/1999 | Juhasz et al. |
| 6,111,645 A | 8/2000 | Tearney et al. |
| 6,315,413 B1 | 11/2001 | Shimmick et al. |
| 8,260,024 B2 | 9/2012 | Farrer et al. |
| 8,394,084 B2 | 3/2013 | Blumenkranz et al. |
| 8,403,921 B2 | 3/2013 | Blumenkranz et al. |
| 8,690,862 B2 | 4/2014 | Palanker et al. |
| 8,709,001 B2 | 4/2014 | Blumenkranz et al. |
| 9,521,949 B2 | 12/2016 | Bor et al. |
| 2009/0247997 A1 | 10/2009 | Watanabe et al. |
| 2011/0172649 A1 | 7/2011 | Schuele et al. |
| 2013/0237970 A1* | 9/2013 | Summers ................. A61F 2/16 606/5 |
| 2014/0135747 A1 | 5/2014 | Donitzky et al. |
| 2015/0374549 A1 | 12/2015 | Scott |
| 2016/0089270 A1* | 3/2016 | Fu ....................... A61F 9/00827 606/5 |
| 2016/0374857 A1 | 12/2016 | Fu et al. |
| 2017/0087021 A1 | 3/2017 | Dishler et al. |

\* cited by examiner

FEMTOSECOND LASER SYSTEM AND METHODS FOR PHOTOREFRACTIVE KERATECTOMY

CROSS REFERENCE TO RELATED APPLICATIONS

This application is a divisional of and claims priority to U.S. patent application Ser. No. 15/795,124, filed Oct. 26, 2017, which is incorporated herein by reference in its entirety.

FIELD OF THE INVENTION

Embodiments of this invention relate generally to laser-assisted ophthalmic procedures, and more particularly, to systems and methods for photorefractive keratectomy with a femtosecond laser system.

BACKGROUND OF THE INVENTION

Photorefractive Keratectomy (PRK) utilizes an excimer laser to change the shape of the cornea. In typical PRK procedures, the corneal epithelium in the ablation zone is first removed to allow for accurate ablation of the of the stromal tissue. This is often accomplished by placing a circular well over the ablation zone and filling it with 20% absolute alcohol for 20-45 s. Once the epithelium is loosened, it can be removed with a week-cell sponge. Other debridement techniques include using a sharp blade, blunt spatula, or rotary brush. The excimer laser is then applied to the exposed corneal stroma. Following the treatment, a (Bandage Contact Lens) BCL is then placed over the cornea. Topical antibiotic, NSAIDs, and corticosteroid are administered postoperatively. Visual acuity slowly improves after the epithelium heals and the refractive state stabilizes 3-6 months following surgery.

While the final visual acuity results of PRK surgery are comparable to LASIK outcomes, PRK visual recovery is initially slower because it takes weeks for the epithelial layer to regenerate and form a stable refractive corneal surface. The entire thickness of the underlying stroma is available for treatment because a flap, including the epithelium and anterior stroma is not removed.

Another disadvantage of traditional excimer laser based systems is that the ablation rate is sensitive to the moisture content of the tissue. As such, longer procedures have less predictability because the longer the laser fires can cause the moisture content of a portion of the tissue to decrease. As such, the depth per pulse may vary throughout the procedure, resulting in inaccurate refractive corrections.

In LASIK, a corneal suction ring is first applied to the topically anesthetized eye. Traditionally, a microketome was used to create a 300 degree flap of corneal tissue by creating an incision along the corneal stoma lamellae to separate the epithelium, Bowman's layer and the anterior stroma from the rest of the remaining posterior stoma. More recently, the femtosecond laser has been commonly used to create this flap. The laser has allowed surgeons to optimize flap dimensions and create a more precise flap. The flap is then reflected back at the hinge, the 60 degree that was not incised, to reveal the stroma.

Next, the excimer laser is used to reshape the residual corneal stromal bed using precisely guided pulses to disrupt the stromal-carbon bonds. The UV laser energy can be titrated to the predetermined depth, which makes it ideal for manipulating the surface of the stroma. Once the stroma has been ablated to achieve the intended optical shift, the corneal flap is then reflated and repositioned on the stromal bed. Healing then takes place over the next several days to weeks.

There are two type of reparative stromal wound healing responses associated with LASIK surgery: a hypercellular fibrotic scar at the flap-wound margin and a weaker transparent, hypocellular primitive scar that develops without reconnection of severed collagen lamella. This hypocellular scar regains only 2.4% of normal stromal strength without evident of remodeling even 6.5 years after LASIK surgery. The hypercelluar scar heals in a more complete manner, averaging about 28% of the normal corneal stromal strength. While it is most vulnerable for spontaneous dislocation during the period immediately following surgery, the corneal flap created in LASIK is at a risk for dislocation at any time following ocular trauma secondary to the limited healing at the flap-stromal interface.

PRK differs from LASIK in that there is no flap creation.

SUMMARY OF THE INVENTION

In light of the shortcomings of both LASIK and prior PRK procedures, there is a need for improved photorefractive therapies that avoid the risks associated with spontaneous flap dislocation, increase the accuracy of refractive correction and decrease discomfort and healing times associated with traditional PRK.

Femtosecond lasers have evolved so that they can create more sophisticated cuts. Instead of using an excimer laser based system and removing the tissue by photoablation, the femtosecond laser systems and methods of the present invention perform an incision configured to form a lenticule comprised of both a stromal portion having the same optical properties as the removed tissue in traditional PRK and an epithelial portion that overlays the stromal portion. Following formation of the lenticule, tweezers and/or other instruments can be used to remove the lenticule from of the eye.

The femtosecond laser procedures described herein have the same effect as PRK but without the necessity of first removing an epithelial layer portion and without photoablation.

One advantage of the present invention is that it minimizes disruption to epithelial layer. In the present invention, the area of the epithelium removed exactly matches the region of the stroma that you are removing. This reduces the area of epithelial layer being removed and therefore affects a smaller portion of the epithelial layer than traditional PRK. Typically, the smaller the area of the epithelial layer removed, the less discomfort and less postoperative healing time is required. As such, the methods and systems of the present invention can decrease comfort and increase healing time relative to traditional PRK. This may be referred to as "epithelial layer sparing" are the two advantages that would be achieved by this invention. Thus creating a clinical benefit.

Another advantage of the present invention versus traditional PRK is that it saves time by doing a single cut. There is no need to remove a portion of the epithelium first, such as by an alcohol well and debridement, and then to ablate the cornea using the excimer laser. Thus, the present invention eliminates the need for a flap cutter system and method.

Another advantage may be increased precision and/or precision of the refractive corrections. In this procedure, incisions are made with the femtosecond laser below the ocular surface, so the cornea does not lose moisture. So the fixed and enclosed system prevents the environment moisture loss made during traditional PRK procedures, and so can increase the accuracy of the refractive correction.

This summary and the following detailed description are merely exemplary, illustrative, and explanatory, and are not intended to limit, but to provide further explanation of the invention as claimed. Additional features and advantages of the invention will be set forth in the descriptions that follow, and in part will be apparent from the description, or may be learned by practice of the invention. The objectives and other advantages of the invention will be realized and attained by the structure particularly pointed out in the written description, claims and the appended drawings.

BRIEF DESCRIPTION OF THE DRAWINGS

The novel features of the invention are set forth with particularity in the appended claims. A better understanding of the features and advantages will be facilitated by referring to the following detailed description that sets forth illustrative embodiments using principles of the invention, as well as to the accompanying drawings, in which like numerals refer to like parts throughout the different views. Like parts, however, do not always have like reference numerals. Further, the drawings are not drawn to scale, and emphasis has instead been placed on illustrating the principles of the invention. All illustrations are intended to convey concepts, where relative sizes, shapes, and other detailed attributes may be illustrated schematically rather than depicted literally or precisely.

DETAILED DESCRIPTION OF THE PREFERRED EMBODIMENTS

Embodiments of this invention are generally directed to systems and methods for laser-assisted ophthalmic procedures, and more particularly, to systems and methods for lenticular laser incisions.

Figure 1:
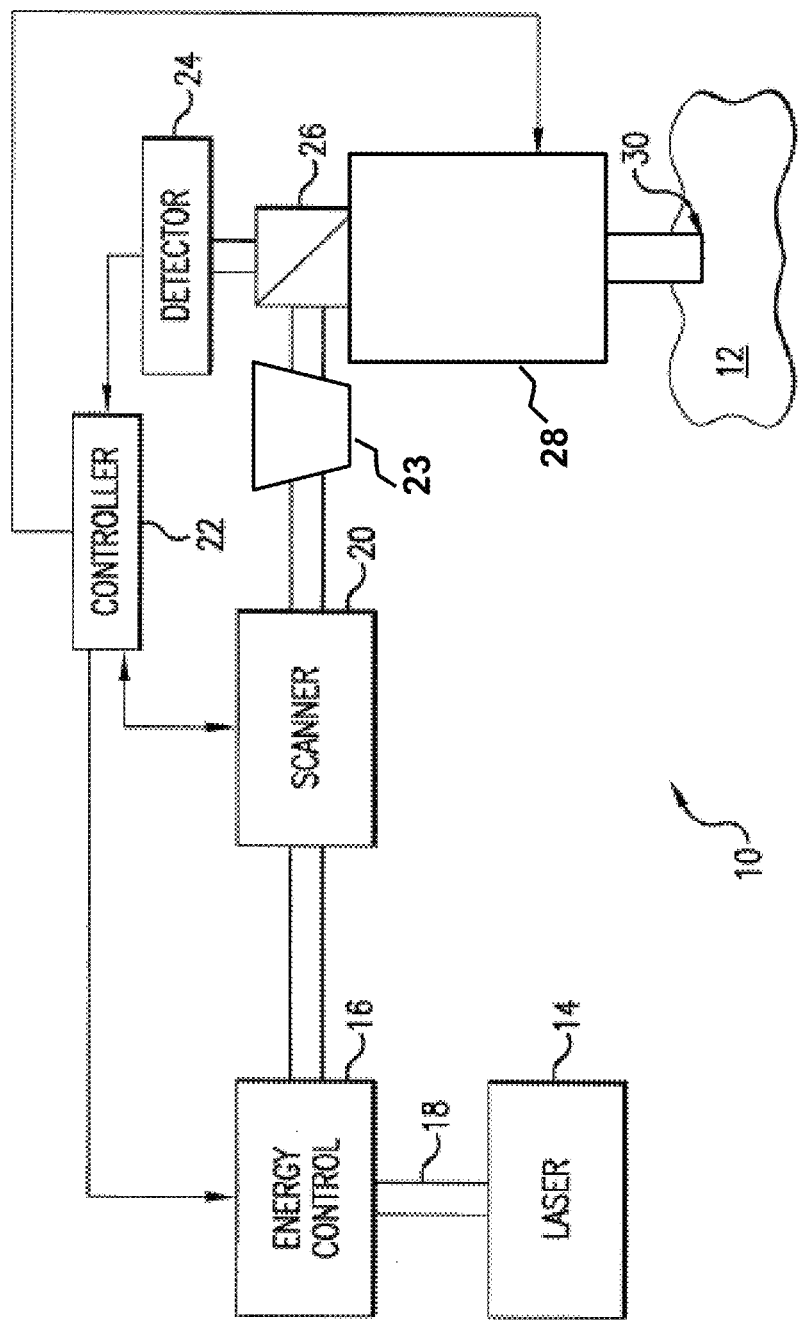
FIG. 1 is a simplified diagram of a surgical ophthalmic laser system according to an embodiment of the present invention.

Referring to the drawings, FIG. 1 shows a system 10 for making an incision in a material 12. The system 10 includes, but is not limited to, a laser 14 capable of generating a pulsed laser beam 18, an energy control module 16 for varying the pulse energy of the pulsed laser beam 18, a Z-scanner 20 for modifying the depth of the pulse laser beam 18, a controller 22, a prism 23 (e.g., a Dove or Pechan prism, or the like), and an XY-scanner 28 for deflecting or directing the pulsed laser beam 18 from the laser 14 on or within the material 12. The controller 22, such as a processor operating suitable control software, is operatively coupled with the Z-scanner 20, the XY-scanner 28, and the energy control unit 16 to direct a scan line 30 of the pulsed laser beam along a scan pattern on or in the material 12. In this embodiment, the system 10 further includes a beam splitter 26 and a detector 24 coupled to the controller 22 for a feedback control mechanism (not shown) of the pulsed laser beam 18. Other feedback methods may also be used, including but not necessarily limited to position encoder on the scanner 20, or the like. In an embodiment, the pattern of pulses may be summarized in machine readable data of tangible storage media in the form of a treatment table. The treatment table may be adjusted according to feedback input into the controller 22 from an automated image analysis system in response to feedback data provided from an ablation monitoring system feedback system (not shown). Optionally, the feedback may be manually entered into the controller 22 by a system operator. The feedback may also be provided by integrating a wavefront measurement system (not shown) with the laser surgery system 10. The controller 22 may continue and/or terminate a sculpting or incision in response to the feedback, and may also modify the planned sculpting or incision based at least in part on the feedback. Measurement and imaging systems are further described in U.S. Pat. Nos. 6,315,413 and 8,260,024, the complete disclosures of which are incorporated herein by reference.

In an embodiment, the system 10 uses a pair of scanning mirrors or other optics (not shown) to angularly deflect and scan the pulsed laser beam 18. For example, scanning mirrors driven by galvanometers may be employed where each of the mirrors scans the pulsed laser beam 18 along one of two orthogonal axes. A focusing objective (not shown), whether one lens or several lenses, images the pulsed laser beam 18 onto a focal plane of the system 10. The focal point of the pulsed laser beam 18 may thus be scanned in two dimensions (e.g., the x-axis and the y-axis) within the focal plane of the system 10. Scanning along the third dimension, i.e., moving the focal plane along an optical axis (e.g., the z-axis), may be achieved by moving the focusing objective, or one or more lenses within the focusing objective, along the optical axis.

Laser 14 may comprise a femtosecond laser capable of providing pulsed laser beams, which may be used in optical procedures, such as localized photodisruption (e.g., laser induced optical breakdown). Localized photodisruptions can be placed at or below the surface of the material to produce high-precision material processing. For example, a micro-optics scanning system may be used to scan the pulsed laser beam to produce an incision in the material, create a flap of the material, create a pocket within the material, form removable structures of the material, and the like. The term "scan" or "scanning" refers to the movement of the focal point of the pulsed laser beam along a desired path or in a desired pattern.

In other embodiments, the laser 14 may comprise a laser source configured to deliver an ultraviolet laser beam comprising a plurality of ultraviolet laser pulses capable of photodecomposing one or more intraocular targets within the eye.

Although the laser system 10 may be used to photoalter a variety of materials (e.g., organic, inorganic, or a combination thereof), the laser system 10 is suitable for ophthalmic applications in some embodiments. In these cases, the focusing optics direct the pulsed laser beam 18 toward an eye (for example, onto or into a cornea) for plasma mediated (for example, non-UV) photoablation of superficial tissue, or into the stroma of the cornea for intrastromal photodisruption of tissue. In these embodiments, the surgical laser system 10 may also include a lens to change the shape (for example, flatten or curve) of the cornea prior to scanning the pulsed laser beam 18 toward the eye.

The laser system 10 is capable of generating the pulsed laser beam 18 with physical characteristics similar to those of the laser beams generated by a laser system disclosed in U.S. Pat. Nos. 4,764,930, 5,993,438, and U.S. patent application Ser. No. 12/987,069, filed Jan. 7, 2011, which are incorporated herein by reference.

Figure 2:
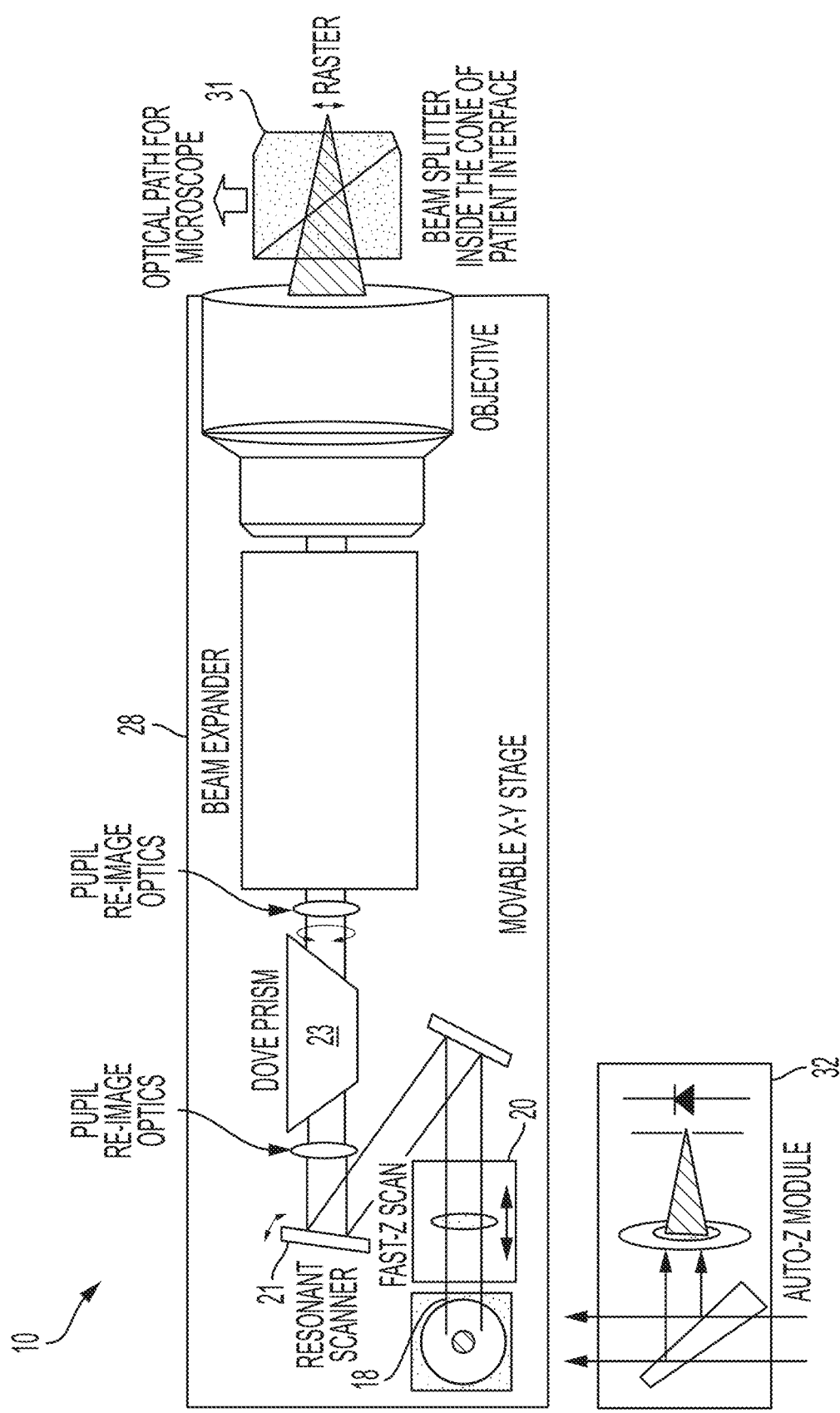
FIG. 2 is another simplified diagram of a surgical ophthalmic laser system according to an embodiment of the present invention.
Figure 3:
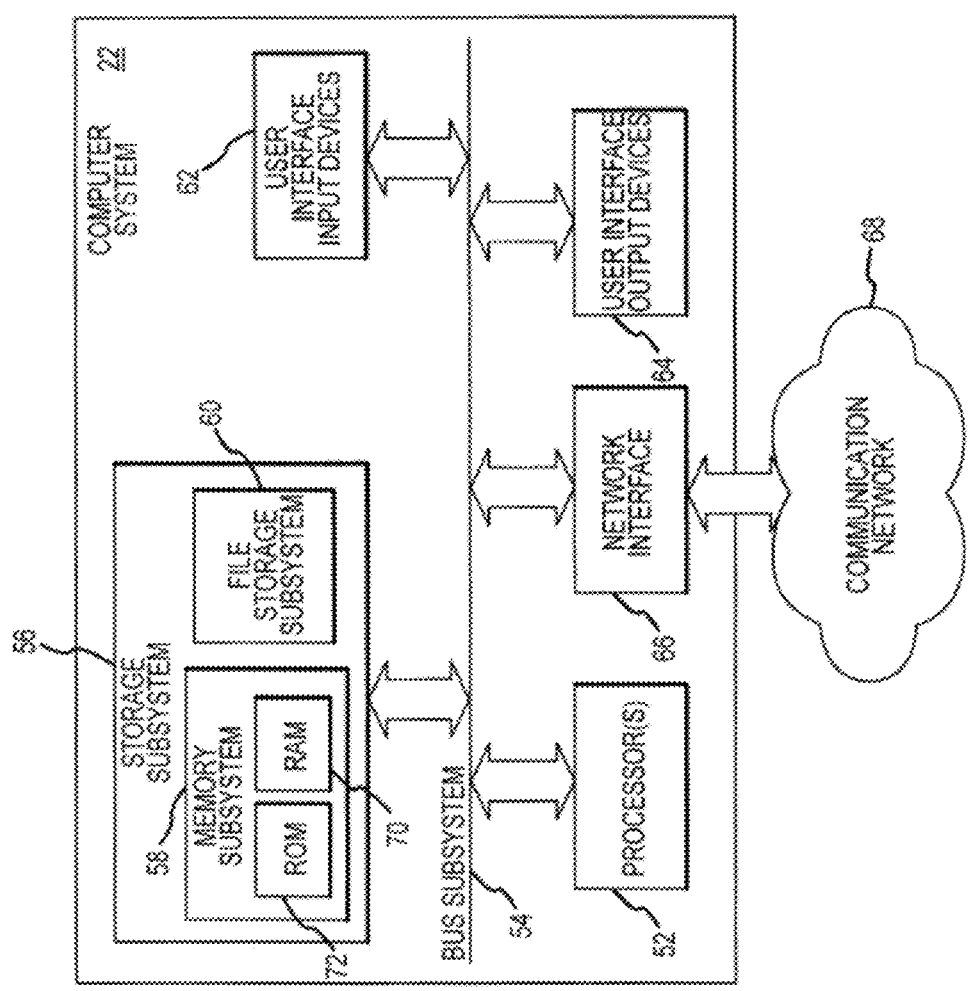
FIG. 3 is a simplified diagram of a controller of a surgical ophthalmic laser system according to an embodiment of the present invention.

FIG. 2 shows another exemplary diagram of the laser system 10. FIG. 3 shows a moveable XY-scanner (or XY-stage) 28 of a miniaturized femtosecond laser system. In this embodiment, the system 10 uses a femtosecond oscillator, or a fiber oscillator-based low energy laser. This allows the laser to be made much smaller. The laser-tissue interaction is in the low-density-plasma mode. An exemplary set of laser parameters for such lasers include pulse energy in the 50-100 nJ range and pulse repetitive rates (or "rep rates") in the 5-20 MHz range. A fast-Z scanner 20 and a resonant scanner 21 direct the laser beam 18 to the prism 23. When used in an ophthalmic procedure, the system 10 also includes a patient interface 31 design that has a fixed cone nose and a portion that engages with the patient's eye. A beam splitter is placed inside the cone of the patient interface to allow the whole eye to be imaged via visualization optics. In one embodiment, the system 10 uses: optics with a 0.6 numerical aperture (NA) which would produce 1.1 μm Full Width at Half Maximum (FWHM) focus spot size; and a resonant scanner 21 that produces 1-2 mm scan line with the XY-scanner scanning the resonant scan line to a 10 mm field. The prism 23 rotates the resonant scan line in any direction on the XY plane. The fast-Z scanner 20 sets the incision depth and produces a side cut. The system 10 may also include an auto-Z module 32 to provide depth reference. The miniaturized femtosecond laser system 10 may be a desktop system so that the patient sits upright while being under treatment. This eliminates the need of certain opto-mechanical arm mechanism(s), and greatly reduces the complexity, size, and weight of the laser system. Alternatively, the miniaturized laser system may be designed as a conventional femtosecond laser system, where the patient is treated while lying down.

FIG. 3 illustrates a simplified block diagram of an exemplary controller 22 that may be used by the laser system 10 according to an embodiment of this invention. Controller 22 typically includes at least one processor 52 which may communicate with a number of peripheral devices via a bus subsystem 54. These peripheral devices may include a storage subsystem 56, comprising a memory subsystem 58 and a file storage subsystem 60, user interface input devices 62, user interface output devices 64, and a network interface subsystem 66. Network interface subsystem 66 provides an interface to outside networks 68 and/or other devices. Network interface subsystem 66 includes one or more interfaces known in the arts, such as LAN, WLAN, Bluetooth, other wire and wireless interfaces, and so on.

User interface input devices 62 may include a keyboard, pointing devices such as a mouse, trackball, touch pad, or graphics tablet, a scanner, foot pedals, a joystick, a touch screen incorporated into a display, audio input devices such as voice recognition systems, microphones, and other types of input devices. In general, the term "input device" is intended to include a variety of conventional and proprietary devices and ways to input information into controller 22.

User interface output devices 64 may include a display subsystem, a printer, a fax machine, or non-visual displays such as audio output devices. The display subsystem may be a flat-panel device such as a liquid crystal display (LCD), a light emitting diode (LED) display, a touchscreen display, or the like. The display subsystem may also provide a non-visual display such as via audio output devices. In general, the term "output device" is intended to include a variety of conventional and proprietary devices and ways to output information from controller 22 to a user.

Storage subsystem 56 can store the basic programming and data constructs that provide the functionality of the various embodiments of the present invention. For example, a database and modules implementing the functionality of the methods of the present invention, as described herein, may be stored in storage subsystem 56. These software modules are generally executed by processor 52. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files. File storage subsystem 60 may include a hard disk drive along with associated removable media, a Compact Disk (CD) drive, an optical drive, DVD, solid-state memory, and/or other removable media. One or more of the drives may be located at remote locations on other connected computers at other sites coupled to controller 22. The modules implementing the functionality of the present invention may be stored by file storage subsystem 60.

Bus subsystem 54 provides a mechanism for letting the various components and subsystems of controller 22 communicate with each other as intended. The various subsystems and components of controller 22 need not be at the same physical location but may be distributed at various locations within a distributed network. Although bus subsystem 54 is shown schematically as a single bus, alternate embodiments of the bus subsystem may utilize multiple busses.

Due to the ever-changing nature of computers and networks, the description of controller 22 depicted in FIG. 3 is intended only as an example for purposes of illustrating only one embodiment of the present invention. Many other configurations of controller 22, having more or fewer components than those depicted in FIG. 3, are possible.

As should be understood by those of skill in the art, additional components and subsystems may be included with laser system 10. For example, spatial and/or temporal integrators may be included to control the distribution of energy within the laser beam, as described in U.S. Pat. No. 5,646,791, which is incorporated herein by reference. Ablation effluent evacuators/filters, aspirators, and other ancillary components of the surgical laser system are known in the art, and may be included in the system. In addition, an imaging device or system may be used to guide the laser beam.

Further details of suitable components of subsystems that can be incorporated into an ophthalmic laser system for performing the procedures described here can be found in commonly-assigned U.S. Pat. Nos. 4,665,913, 4,669,466, U.S.

U.S. Pat. Nos. 4,732,148, 4,770,172, 4,773,414, 5,207,668, 5,108,388, 5,219,343, 5,646,791, 5,163,934, 8,394,084, 8,403,921, 8,690,862, 8,709,001, U.S. application Ser. No. 12/987,069, filed Jan. 7, 2011, and U.S. application Ser. No. 13/798,457 filed Mar. 13, 2013, which are incorporated herein by reference.

In an embodiment, the laser surgery system 10 includes a femtosecond oscillator-based laser operating in the MHz range, for example, 10 MHz, for example, from several MHz to tens of MHz. For ophthalmic applications, the XY-scanner 28 may utilize a pair of scanning mirrors or other optics (not shown) to angularly deflect and scan the pulsed laser beam 18. For example, scanning mirrors driven by galvanometers may be employed, each scanning the pulsed laser beam 18 along one of two orthogonal axes. A focusing objective (not shown), whether one lens or several lenses, images the pulsed laser beam onto a focal plane of the laser surgery system 10. The focal point of the pulsed laser beam 18 may thus be scanned in two dimensions (e.g., the X-axis and the Y-axis) within the focal plane of the laser surgery system 10. Scanning along a third dimension, i.e., moving the focal plane along an optical axis (e.g., the Z-axis), may be achieved by moving the focusing objective, or one or more lenses within the focusing objective, along the optical axis. It is noted that in many embodiments, the XY-scanner 28 deflects the pulse laser beam 18 to form a scan line.

Figure 4:
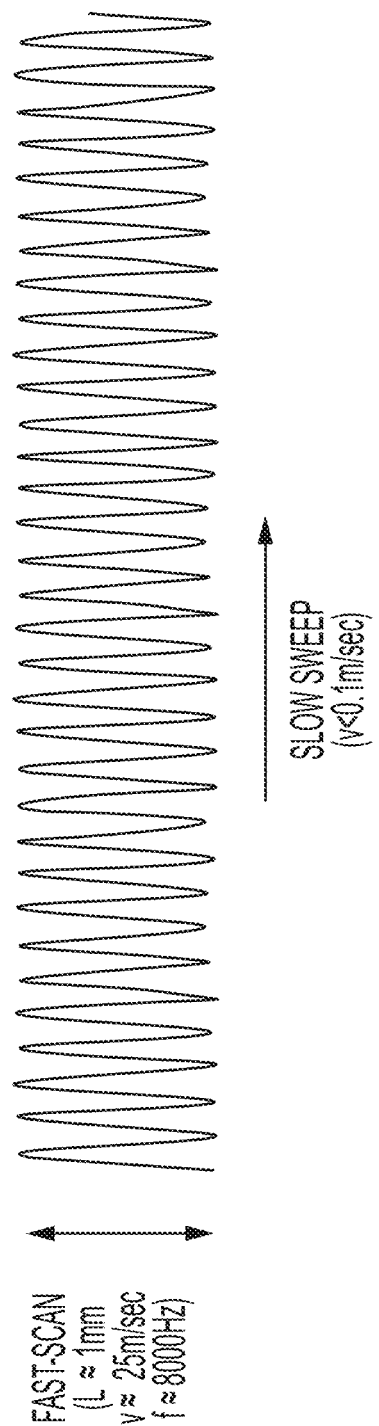
FIG. 4 illustrates an exemplary scanning of a surgical ophthalmic laser system according to an embodiment of the present invention.

In other embodiments, the beam scanning can be realized with a "fast-scan-slow-sweep" scanning scheme. The scheme consists of two scanning mechanisms: first, a high frequency fast scanner is used to produce a short, fast scan line (e.g., a resonant scanner 21 of FIG. 2); second, the fast scan line is slowly swept by much slower X. Y, and Z scan mechanisms. FIG. 4 illustrates a scanning example of a laser system 10 using an 8 kHz resonant scanner 21 to produce a scan line of about 1 mm and a scan speed of about 25 m/sec, and X, Y, and Z scan mechanisms with the scan speed smaller than 0.1 m/sec. The fast scan line may be perpendicular to the optical beam propagation direction, i.e., it is always parallel to the XY plane. The trajectory of the slow sweep can be any three dimensional curve drawn by the X, Y, and Z scanning devices (e.g., XY-scanner 28 and Z-scanner 20). An advantage of the "fast-scan-slow-sweep" scanning scheme is that it only uses small field optics (e.g., a field diameter of 1.5 mm) which can achieve high focus quality at relatively low cost. The large surgical field (e.g., a field diameter of 10 mm or greater) is achieved with the XY-scanner, which may be unlimited.

Figure 5:
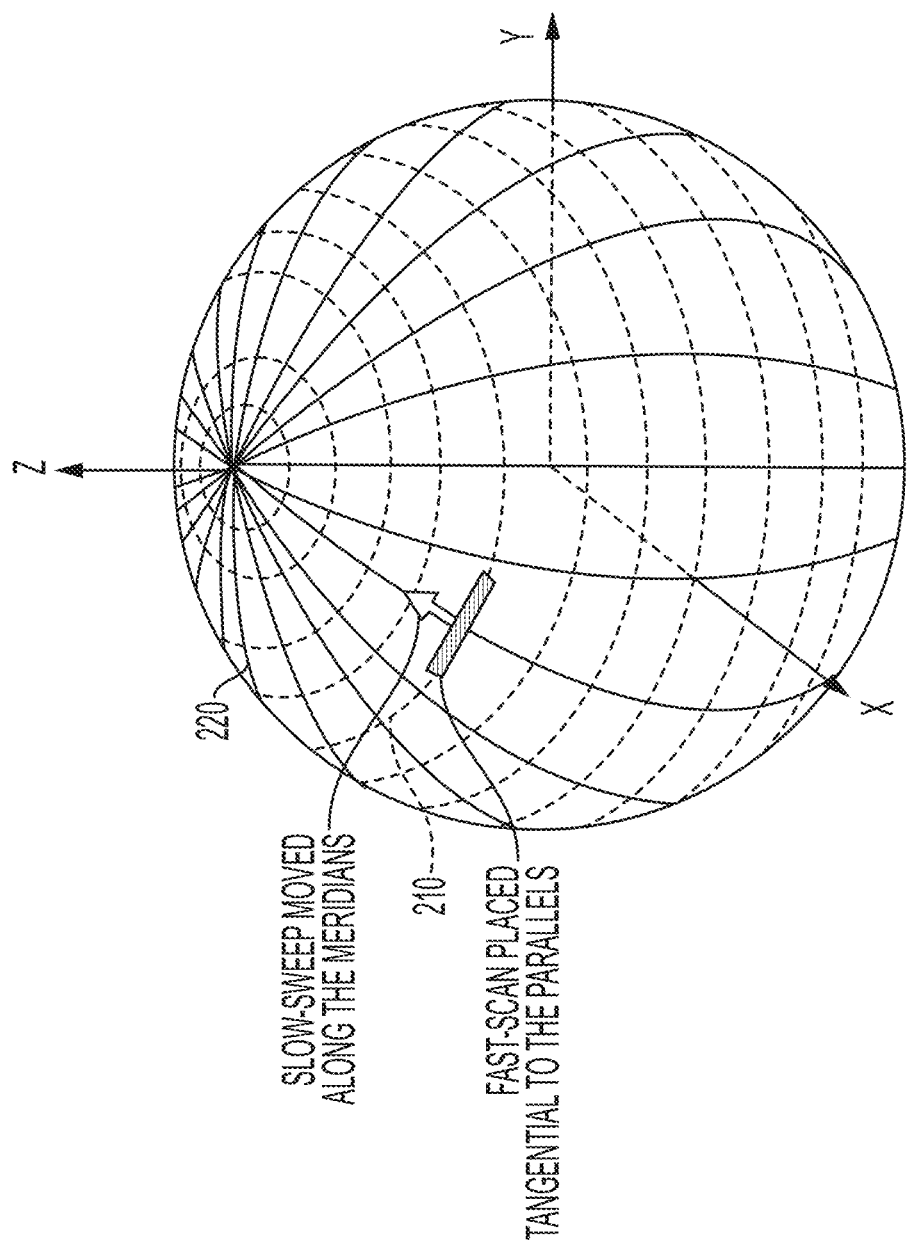
FIG. 5 illustrates an exemplary lenticular incision using a fast-scan-slow-sweep scheme of a surgical ophthalmic laser system according to an embodiment of the present invention.

In another embodiment shown in FIG. 5, the laser system 10 creates a smooth lenticular cut using the "fast-scan-slow-sweep" scanning scheme under a preferred procedure. First, in a three dimensional lenticular cut, the fast scan line is preferably placed tangential to the parallels of latitude 210. For example, in the miniaturized flap maker laser system 10 of FIG. 2, this can be realized by adjusting a prism 23 to the corresponding orientations via software, e.g., via the controller 22. Second, the slow sweep trajectory preferably moves along the meridians of longitude 220. For example, in the miniaturized flap maker system of FIG. 2, this can be done by coordinating the XY scanner 28, and the Fast-Z scanner 20 via the software, e.g., via the controller 22. The procedure starts with the scan line being parallel to the XY plane, and sweeps through the apex of the lens, following the curvature with the largest diameter With this preferred procedure, there are no vertical "steps" in the dissection, and vertical side cuts are eliminated. As will be analyzed herein below, the deviations between the laser focus locations and the intended spherical surface dissections are also minimized.

Figure 6:
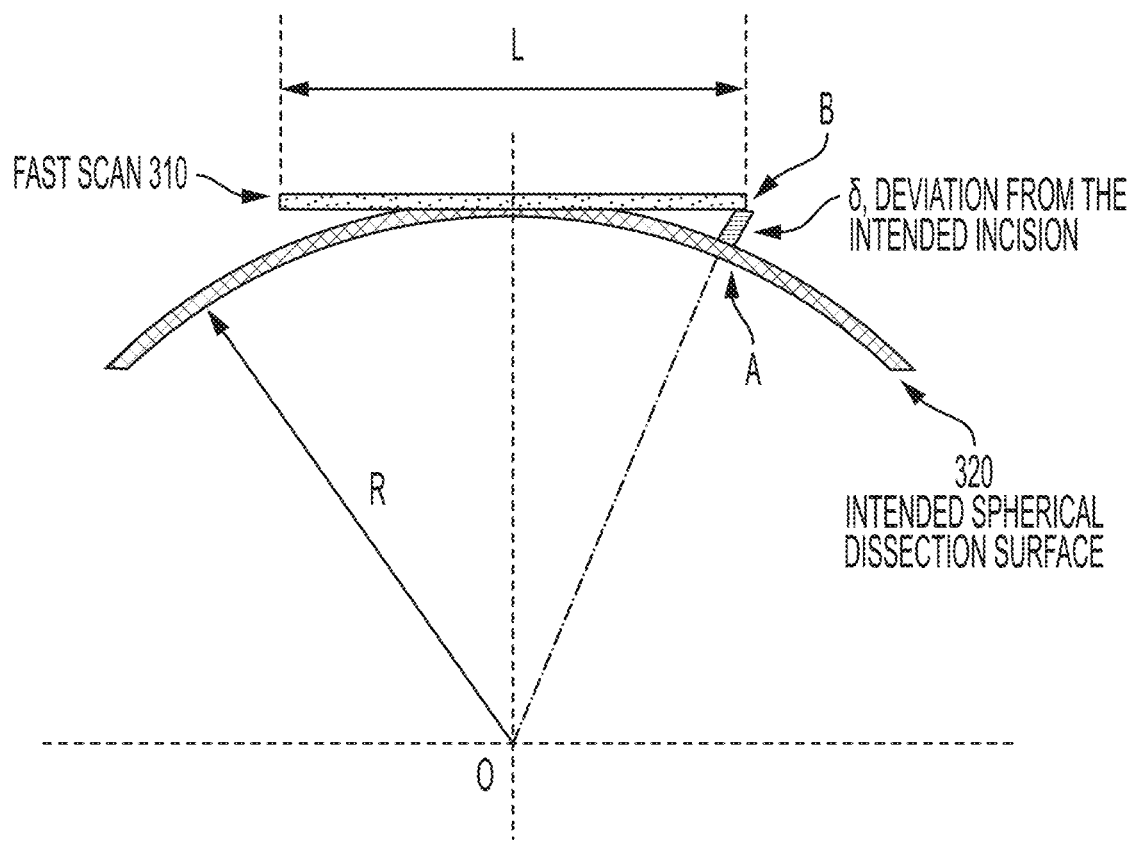
FIG. 6 illustrates a geometric relation between a fast scan line and an intended spherical dissection surface of a surgical ophthalmic laser system according to an embodiment of the present invention.

FIG. 6 shows the geometric relation between the fast scan line 310 and the intended spherical dissection surface 320, e.g., of a lens, especially the distance deviation (8) between the end point B of the scan line 320 and point A on the intended dissection surface 320. The maximum deviation 8 is the distance between point A and point B, and is given by $$\delta = \sqrt{R^2 + \frac{L^2}{4}} - R = \frac{L^2}{8R}, \qquad \text{equation (1)}$$

where R is greater than L. R is the radius of curvature of the surface dissection 320, and L is the length of the fast scan.

In an exemplary case of myopic correction, the radius of curvature of the surface dissection may be determined by the amount of correction, $\Delta D$, using the following equation $$\Delta D = \frac{(n-1)}{R_1} + \frac{(n-1)}{R_2}, \qquad \text{equation (2)}$$

where n=1.376, which is the refractive index of cornea, and $R_1$ and $R_2$ (may also be referred herein as $R_t$ and $R_b$) are the radii of curvature for the top surface and bottom surface of a lenticular incision, respectively. For a lenticular incision with $R_1=R_2=R$ (the two dissection surface are equal for them to physically match and be in contact), we have $$R = \frac{2(n-1)}{\Delta D}, \qquad \text{equation (3)}$$

Figure 7:
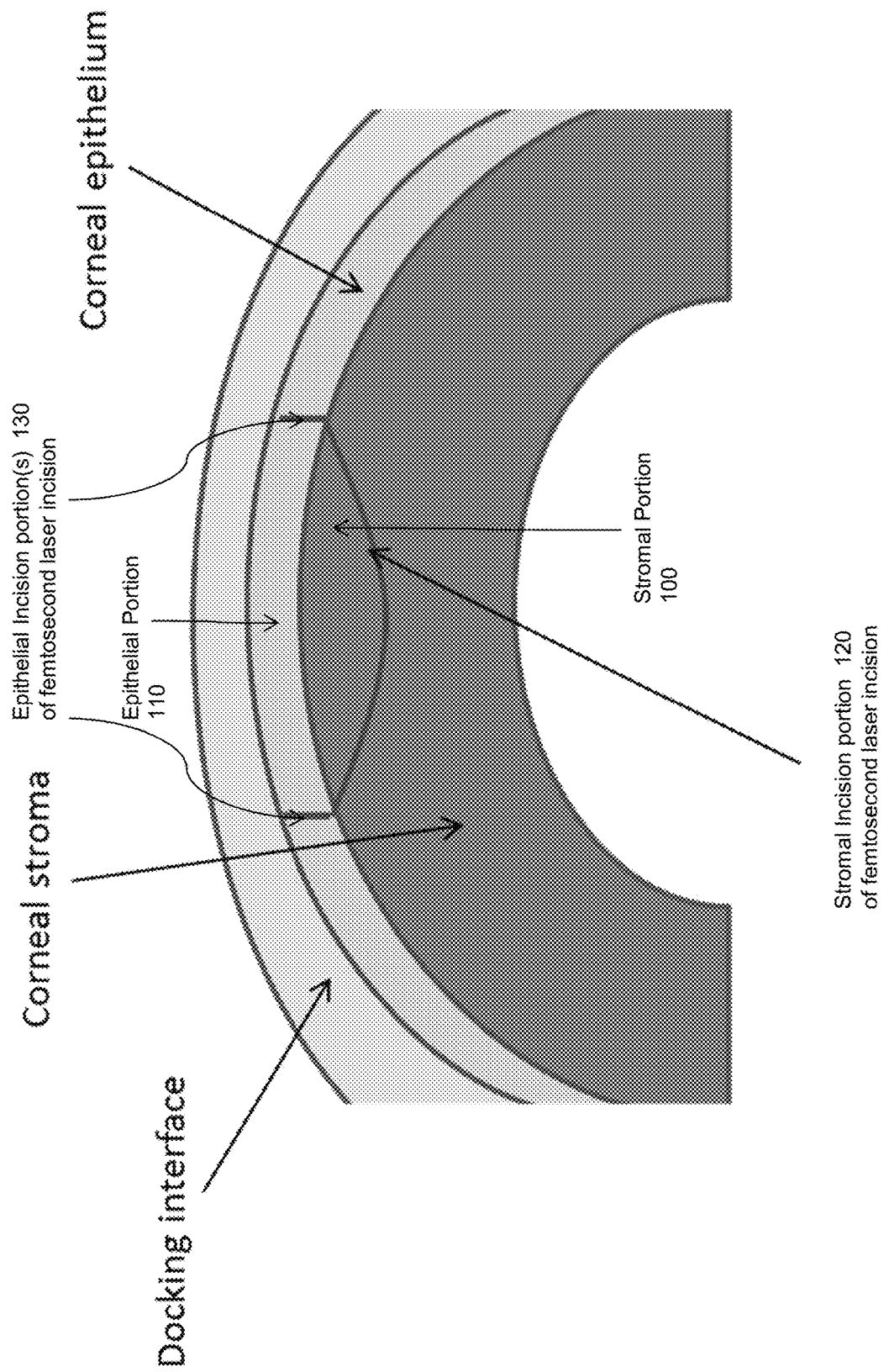
FIG. 7 is a graphical illustration of one embodiment of the incisions made by the ophthalmic laser surgical system and methods for performing photorefractive keratectomy according to the present invention.

In some embodiments, the femtosecond laser system and associated methods of the present invention carry out scanning patterns that are configured to form and do form the femtosecond laser incision shown in the embodiment of FIG. 7.

Figure 8:
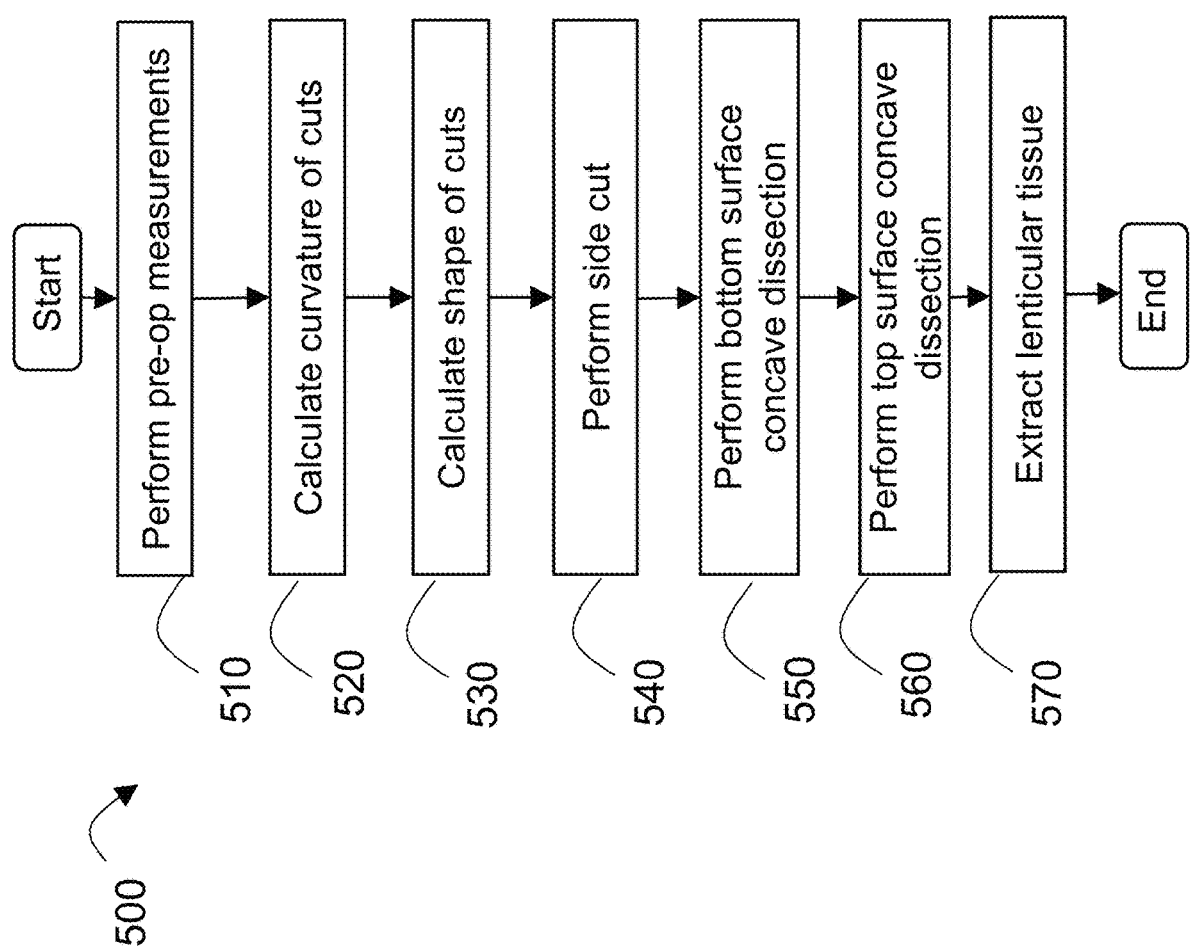
FIG. 8 is a flowchart illustrating an exemplary surgery process according to an embodiment of the present invention.

As shown in FIG. 7, a femtosecond laser incision 115 according to the present invention comprises a stromal incision portion 120 and a epithelial incision portion(s) 130. The epithelial incision portion(s) 130 is disposed from the upper epithelial surface to the upper surface of the corneal stroma the stromal incision portion 120 transects the corneal stroma. Together the epithelial incision portion(s) 130 and stromal incision portion 120 define a lenticule comprising the stromal portion 100 shaped for achieving the predetermined refractive and the epithelium portion 130 overlaying the stromal portion 100. As shown in FIG. 8, the stromal portion 100 and the epithelium portion 130 overlaying the stromal portion 100 the lenticule remain connected at the epithelial layer/corneal stroma interface and may therefore be removed together after completion of the femtosecond laser incision.

The incisions of the present invention may be conducted by deflecting the pulsed femtosecond laser beam in one or more scanning patterns in the corneal stroma and corneal epithelium of the eye of the patent. The one or more scanning patterns are preferably raster scans. More preferably, the incision is performed in a single scanning pattern, preferably a single raster scan. Preferably the scanning patterns (and resulting incisions) of the present invention are performed by the laser surgical system and methods of the present invention as a single incision pattern configured to separate both the stromal portion 100 and the overlaying epithelial portion 110 from the underlying portions of the of the eye of the patient. Thereafter, one can remove both the stromal portion 100 and epithelial portion 110 from the eye with tweezers (or by other suitable methods). The amount of the epithelial layer saved may be about 1 mm2 smaller than traditional PRK procedure.

The size and shape of the stromal portion 100 and the corresponding size and shape of the stromal incision portion 120 may be based on any methods known to those ordinarily skilled in the art for producing a predetermined refractive correction. For instance, a refractive correction for a patient can be determined based on wavefront measurement, corneal topography, manifest refraction, Optical Coherence Tomography (OCT) or some combination of these diagnostic modalities. In many embodiments, an algorithm the same or similar to the ones for LASIK or PRK known to those ordinarily skilled is used to determine the size and shape of ophthalmic tissue to be removed at any given location on the stroma based on the optical zone chosen and the transition zone. For instance, in algorithms based on manifest refraction, the size and shape of the stromal portion 100 may be a disc shape based on a shape of the corresponding contact lens for that manifest refraction.

In many embodiments, the stromal portion 100 is the same size and shape as the stromal tissue that would have been removed by photoablation in traditional PRK methods. The depth of the stromal incision is generally related to the amount of correction, with a typical rule of thumb being 13 microns per diopter, which depends on the sizer of the optical zone and ablation zone.

The epithelial incision portion 130 should be sized and shaped to completely separate the epithelial portion 110 from the remainder of the corneal epithelium. The epithelial incision portion 130 should therefore completely transect the corneal epithelium in the depth direction and should be disposed from the upper surface of the corneal epithelium to the upper surface of the stroma in the depth direction. The depth of the corneal epithelium in the depth direction is about 50 microns.

The epithelial incision portion 130 should also be shaped so that at least a portion of the top surface of the epithelium portion is open to the ambient environment to allow direct access to the lenticule by tweezers or another removal apparatus. The top surface of the lenticule (i.e. the top surface of epithelial portion 130) should not be completely enclosed within the corneal epithelium. The epithelial portion 130 should be sized so as to reduce or minimize the size of the corneal epithelium removed during the photoreactive procedure. In some embodiments, the top and bottom surface of the epithelial portion 130 will be sized substantially the same as the upper surface of the stromal portion 110. Alternatively, the size of the corneal epithelium may be reduced by shaping the epithelial incision portion 130 so that it extends inwardly towards a center of epithelial portion in a direction from the upper surface of the stromal portion 100 to the upper surface of the epithelial portion 110. The epithelial incision portion 130 is shaped so that it extends outwardly away from a center of epithelial portion in a direction from the upper surface of the stromal portion 100 to the upper surface of the epithelial portion 110. This may facilitate easy removal of the lenticule at the cost of increasing an amounts of corneal epithelium removed relative to other embodiments.

The order of making the epithelial incision portion(s) 130 and the stromal incision portion 120 is not particularly limited. However, in some embodiments, the laser system will perform the stromal incision portion 120 first followed by the epithelial incisions portion 130 to detach the removed tissue lenticule from the eye.

In many embodiment, the laser systems and methods of the present invention will include a patient interface. The patent invention may be an applanating patient interface, a non-applanating patent interface or a liquid surface interface. In some embodiments, the methods may be done without a patient interface but with suitable eye tracking.

In many embodiments the femtosecond laser would use manual or automated alignment determined by the location of various ocular landmarks for registering the correction onto the eye. The ocular landmarks may include the outer iris boundary, the pupil and the corneal vertex.

Further, the system and methods of the present invention may typically include an eye registration system compare orientation and rotation of the eye during the laser ophthalmic procedure with the pre-operative diagnostic measurement. In one embodiment, the registration system comprises iris registration. In general, iris registration compares the an image of the eye taken at time of pre-operative diagnostic measurements with an image taken at or during the laser ophthalmic procedure orient the laser and how to center the treatment patterns.

Following the removal of the stromal and epithelium layer portions, the methods and systems of the present invention may include postoperative healing methods such as those used in prior art PRK procedures suitable to re-grow the epithelial layer removed during the laser surgical procedure. For instance, a BCL (Bandage Contact Lens) may be placed over the cornea, and topical antibiotic, NSAIDs, and corticosteroid may administered postoperatively. Healing then takes place over a period of time after surgery.

FIG. 8 is a flowchart illustrating an exemplary surgery process 1500 according to an embodiment of the present invention. The laser system 10 may start a surgical procedure performing pre-operation measurements (Action Block 510). For example, in an ophthalmologic surgery for hyperopic correction, the hyperopic diopter is determined, the SLOW_Z position is determined, and so on. The laser system 10 calculates a shape of the lenticule to be removed based on the amount of correction, e.g., the hyperopic correction determined in pre-operation measurements (Action Block 520). The laser system 10 the calculates the shape of the incisions (Action Block 530) configured to achieve the predetermined shape of the lenticule. The laser system 10 first performs a epithelial layer incision incision to provide a vent for gas that can be produced in the lenticular surface dissections, and for tissue extraction later on (Action Block 540). The laser system 10 then performs the stromal layer incision portion (Action Block 550). Performing the dissections in this order allows gas to vent out of the cornea instead of becoming trapped in gas bubbles within the cornea. The lenticular tissue is then extracted (Action Block 560).

All patents and patent applications cited herein are hereby incorporated by reference in their entirety.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including." and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

While certain illustrated embodiments of this disclosure have been shown and described in an exemplary form with a certain degree of particularity, those skilled in the art will understand that the embodiments are provided by way of example only, and that various variations can be made without departing from the spirit or scope of the invention. Thus, it is intended that this disclosure cover all modifications, alternative constructions, changes, substitutions, variations, as well as the combinations and arrangements of parts, structures, and steps that come within the spirit and scope of the invention as generally expressed by the following claims and their equivalents.

What is claimed is:

1. A method for performing a photorefractive keratectomy procedure in an eye of a patient, the system comprising:
   generating a femtosecond pulsed laser beam; and
   deflecting the laser beam in an incision scanning pattern which includes an epithelial incision portion that transects an epithelium layer of a cornea of the eye and a stromal incision portion located in a stromal layer of the cornea to form a lenticule, wherein the lenticule is defined by an anterior surface of the cornea, the epithelial incision portion and the stromal incision portion and is separated from underlying and surrounding portions of the cornea, wherein the stromal incision portion is curved, and the stromal incision portion and the epithelial incision portion intersect at an angle relative to each other, and wherein the lenticule comprises both a stromal portion shaped to affect a refractive property of the eye and an epithelial portion overlaying the stromal portion.

2. The method of claim 1, wherein the step of deflecting the laser beam includes using a resonant scanner to scan the pulsed laser beam to form a scan line.

3. The method of claim 2, wherein the step of deflecting the laser beam further includes using a XY-scan device to deflect the scan line.

4. The method of claim 3, wherein the scan line is tangential to the parallels of latitude of the lenticule.

5. The method of claim 4, wherein the scan line is moved along meridians of longitude of the lenticule.

6. The method of claim 4, wherein there is a deviation between an end point of the scan line and a point on the spherical surface of the lenticule.

7. The method of claim 1, wherein the incision scanning pattern is a raster scan.

8. The method of claim 1, wherein the incision scanning patterns is a single raster scan configured to separate both the stromal portion and the overlaying epithelial portion from the underlying portions of the eye of the patient.

9. The method of claim 1, wherein the incision scanning pattern is configured such that both the stromal portion and the epithelial portion are removeable from the eye with tweezers.

10. The method of claim 1, wherein the incision scanning pattern is configured such that the epithelial portion is connected to the stromal portion.

11. The method of claim 1, wherein the stromal portion of the lenticule has a maximum thickness at its center and decreasing thicknesses at positions located at increasing radial distances from the center.

* * * * *